United States Patent
Maggioni

(10) Patent No.: US 7,696,413 B2
(45) Date of Patent: Apr. 13, 2010

(54) RED LEAF LETTUCE VARIETIES

(75) Inventor: Alessandro Maggioni, Fidenza (IT)

(73) Assignee: ISI Sementi-Spa, Fidenza (PR) (IT)

( * ) Notice: Subject to any disclaimer, the term of this patent is extended or adjusted under 35 U.S.C. 154(b) by 15 days.

(21) Appl. No.: 12/052,668

(22) Filed: Mar. 20, 2008

(65) Prior Publication Data

US 2008/0235818 A1  Sep. 25, 2008

Related U.S. Application Data

(60) Provisional application No. 60/919,180, filed on Mar. 20, 2007.

(51) Int. Cl.
*A01H 1/00* (2006.01)
*A01H 5/00* (2006.01)
*A01H 5/10* (2006.01)

(52) U.S. Cl. .................. 800/305; 435/410; 800/260; 800/298

(58) Field of Classification Search .................. None
See application file for complete search history.

(56) References Cited

U.S. PATENT DOCUMENTS 7,371,931 B1 * 5/2008 Knerr .................. 800/305

* cited by examiner

*Primary Examiner*—David H Kruse
(74) *Attorney, Agent, or Firm*—Morrison & Foerster LLP

(57) ABSTRACT

Lettuce varieties ISI 43509 and ISI 43541 are described.

30 Claims, No Drawings

RED LEAF LETTUCE VARIETIES

I. RELATED APPLICATION

This application claims the benefit under 35 USC 119(e) of U.S. Provisional Application No. 60/919,180, filed Mar. 20, 2007, the content of which is hereby incorporated by reference in its entirety.

II. FIELD OF THE INVENTION

The present invention is directed to new varieties of lettuce, *Lactuca sativa*.

III. BACKGROUND OF THE INVENTION

Lettuce is an important crop consumed worldwide. Even though lettuce is a popular crop, there is a need to develop new varieties which display improved characteristics.

IV. SUMMARY OF THE INVENTION

In order to meet these needs, the present invention is directed to improved lettuce varieties. In one embodiment, the present invention is directed to lettuce, *Lactuca sativa*, seed designated as ISI 43509 having ATCC Accession Number X1. In another embodiment, the invention is further directed to a lettuce, *Lactuca sativa* plant and parts isolated therefrom produced by growing ISI 43509 lettuce seed. The present invention is further directed to a *Lactuca sativa* plant and parts isolated therefrom having all the physiological and morphological characteristics of a Lactuca sativa plant produced by growing ISI 43509 lettuce seed having ATCC Accession Number X1. In another embodiment, the present invention is further directed to an $F_1$ hybrid lettuce, *Lactuca sativa* seed, plants grown from the seed and a head isolated therefrom having ISI 43509 as a parent wherein ISI 43509 is grown from ISI 43509 lettuce seed having ATCC Accession Number X1.

Lettuce plant parts include lettuce heads, lettuce leaves, parts of lettuce leaves, pollen, ovules, flowers and the like. In another embodiment, the present invention is further directed to lettuce heads, lettuce leaves, parts of lettuce leaves, flowers, pollen and ovules isolated from ISI 43509 lettuce plants. In another embodiment, the present invention is further directed to tissue culture of ISI 43509 lettuce plants.

In another embodiment, the present invention is further directed to packaging material containing ISI 43509 plant parts. Such packaging material includes but is not limited to boxes, plastic bags, etc. The ISI 43509 plant parts may be combined with lettuce plant parts of other plant varieties.

In another embodiment, the present invention is further directed to a method of selecting lettuce plants comprising a) growing ISI 43509 lettuce plants wherein the ISI 43509 plants are grown from lettuce seed having ATCC Accession Number X1 and b) selecting a plant from step a). In another embodiment, the present invention is further directed to lettuce plants, plant parts and seeds produced by the lettuce plants wherein the lettuce plants are isolated by the selection method of the invention.

In another embodiment, the present invention is further directed to a method of breeding lettuce plants comprising crossing a lettuce plant with a plant grown from ISI 43509 lettuce seed having ATCC Accession Number X1. In another embodiment, the present invention is further directed to lettuce plants, lettuce parts from the lettuce plants and seeds produced therefrom where the lettuce plant is isolated by the breeding method of the invention.

The present invention is further directed to lettuce, *Lactuca sativa*, seed designated as ISI 43541 having ATCC Accession Number X4. In one embodiment, the present invention is further directed to a lettuce, *Lactuca sativa* plant and parts isolated therefrom produced by growing ISI 43541 lettuce seed. In another embodiment, the present invention is further directed to a Lactuca sativa plant and parts isolated therefrom having all the physiological and morphological characteristics of a *Lactuca sativa* plant produced by growing ISI 43541 lettuce seed having ATCC Accession Number X4. In another embodiment, the present invention is further directed to an $F_1$ hybrid lettuce, *Lactuca sativa* seed, plants grown from the seed and a head isolated therefrom having ISI 43541 as a parent wherein ISI 43541 is grown from ISI 43541 lettuce seed having ATCC Accession Number X4.

Lettuce plant parts include lettuce heads, lettuce leaves, parts of lettuce leaves, pollen, ovules, flowers and the like. In another embodiment, the present invention is further directed to lettuce heads, lettuce leaves, parts of lettuce leaves, flowers, pollen and ovules isolated from ISI 43541 lettuce plants. In another embodiment, the present invention is further directed to tissue culture of ISI 43541 lettuce plants.

In another embodiment, the present invention is further directed to packaging material containing ISI 43541 plant parts. Such packaging material includes but is not limited to boxes, plastic bags, etc. The ISI 43541 plant parts may be combined with lettuce plant parts of other plant varieties.

In another embodiment, the present invention is further directed to a method of selecting lettuce plants comprising a) growing ISI 43541 lettuce plants wherein the ISI 43541 plants are grown from lettuce seed having ATCC Accession Number X4 and b) selecting a plant from step a). In another embodiment, the present invention is further directed to lettuce plants, plant parts and seeds produced by the lettuce plants wherein the lettuce plants are isolated by the selection method of the invention.

In another embodiment, the present invention is further directed to a method of breeding lettuce plants comprising crossing a lettuce plant with a plant grown from ISI 43541 lettuce seed having ATCC Accession Number X4. In another embodiment, the present invention is further directed to lettuce plants, lettuce parts from the lettuce plants and seeds produced therefrom where the lettuce plant is isolated by the breeding method of the invention.

V. DETAILED DESCRIPTION OF THE INVENTION

Origin and Breeding History of the Varieties

ISI 43509

ISI 43509 is a red leaf lettuce variety developed from a hand pollinated cross of the varieties ISI 44038 and ISI 43137, both available from our genetical material. The initial cross was made in Fidenza (PR), Italy. The F1 seed harvested was designated as 33-0601070. The cross was made to produce a variety with dark red cherry colour, upright standing, smooth leaves, good resistance against mildew, black seeds.

The following year, approximately 25 plants of the F1 seed were planted in Cesena (FC), Italy for seed increase. The block was roughed eliminating the self pollination plants. The F2 seed was harvested individually.

More than 20 F2 populations were planted in a research and development field trial in Cesena (FC), Italy the following year. Individual F2 plants were selected at market maturity for particular distinguishing characteristics in type, size, dark red cherry colour, days to bolting, upright standing, smooth leaf, resistance against mildew, black seed.

The F3 seed were trialed throughout the growing season in years 3 and 4 in Fidenza (PR), Italy.

A selected line was increased in year 5 in removing early bolting, less darker and bubbled plants and plants susceptible to mildew. The plants were harvested individually and the F5 population showed a good stability and uniformity.

The F6 seed was uniform and without variants and showed good bolting resistance. ISI 43509 was evaluated uniform and stable in commercial trials and seed production for two years.

Objective Description of the Variety ISI 43509

Plant Type

ISI 43509 is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/5×10. The apical margin is moderately dentate. The basal margin is moderately dentate. The undulation is medium. The green color is light green. The distribution of the anthocyanin is throughout and the concentration is intense. Rolling is absent. It is uncupped. There is no reflexing.

Mature Leaves

Margin

The incision depth is absent/shallow. The indentation is shallowly dentate. The undulations of the apical margin are strong. The green color is light green.

The anthocyanin distribution is throughout and the concentration is intense. It is large in size. It is glossy. Blistering is absent/slight. The leaf is thin. The trichomes are absent.

Plant

The spread of frame leaves is 18 cm. The head diameter is 20 cm. The head shape is non-heading. The head firmness is loose. The butt is slightly concave. The midrib is moderately raised. The diameter at base of head is 15 mm. The ratio of head diameter/core diameter is 13.3. The core height from base of head to apex is 36 mm.

Bolting

The number of days from first water date to seed stalk emergence was 40. The bolting class is medium. The height of mature seed stalk is 80. The spread of bolter plant is 35 cm. The bolter leaves are straight. The margin is entire. The color is light green. The bolter habit of the terminal inflorescence is absent. The bolter habit of the lateral shoots is present. The bolter habit of the basal side shoots is absent.

Maturity

The season picked was summer. The earliness of harvest-mature head formation was 24 days.

Adaptation

The primary region of adaptation was Southwest. ISI 43509 adapted in the Southwest in the spring, summer, and fall seasons. The soil type was both organic and mineral.

Viral Diseases

ISI 43509 is moderately susceptible/moderately resistant to big vein, lettuce mosaic, and lettuce infectious yellows. It is susceptible to cucumber mosaic, tomato bushy stunt, turnip mosaic, and beet western yellows.

Fungal/Bacterial Diseases

ISI 43509 is susceptible to bacterial soft rot, botrylis, bacterial leaf spot, and anthracnose. It is moderately susceptible/moderately resistant to corky root rot, powdery mildew, sclerotinla drop, and verticillium wilt. It is resistant to the CAI-CAVI races of downy mildew.

Insects

ISI 43509 is susceptible to cabbage loopers, root aphids, green peach aphid, lettuce aphid, and pea leafminer.

Physiological Stresses

ISI 43509 is susceptible to brown rib. It is moderately susceptible/moderately resistant to cold, tipburn, drought, and salt.

Post Harvest Stress

ISI 43509 is susceptible to pink rib, russet spotting, rusty brown discoloration, internal rib necrosis, and brown stain.

Comparisons to ISI 43509

Lirac

The most similar variety used as a comparison to ISI 43509 is Lirac.

Plant Type

Lirac is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/0×10. The apical margin is moderately dentate. The basal margin is moderately dentate. The undulation is medium. The green color is light green. The distribution of the anthocyanin is throughout. The concentration is moderate. Rolling is absent. It is uncupped. There is no reflexing.

Mature Leaves

Margin

The incision depth is absent/shallow. The indentation is shallowly dentate. The undulations of the apical margin are strong. The green color is light green.

The anthocyanin distribution is throughout and the concentration is moderate. It is medium in size. It is glossy. There is moderate blistering. The leaf is thin. The trichomes are absent.

Plant

The spread of frame leaves is 21 cm. The head diameter is 24 cm. The head shape is non-heading. The head firmness is loose. The butt is slightly concave. The midrib is moderately raised. The diameter at base of head is 14 mm. The ratio of head diameter/core diameter is 17.1. The core height from base of head to apex is 33 mm.

Bolting

The number of days from first water date to seed stalk emergence was 48. The bolting class is slow. The height of mature seed stalk is 65. The spread of bolter plant is 30 cm. The bolter leaves are straight. The margin is entire. The color is light green. The bolter habit of the terminal inflorescence is absent. The bolter habit of the lateral shoots is present. The bolter habit of the basal side shoots is absent.

Maturity

The season picked was summer. The earliness of harvest-mature head formation was 30 days.

Viral Diseases

The Lirac is susceptible to big vein, lettuce mosaic, cucumber mosaic, tomato bushy stunt, turnip mosaic, beet western yellows and lettuce infectious yellows.

Fungal/Bacterial Diseases

The Lirac is susceptible to corky root rot, botrylis, verticillium wilt, bacterial leaf spot, and anthracnose, powdery mildew, sclerotinla drop, and bacterial soft rot. It is moderately resistant/moderately susceptible to CAI-CAVI races of downy mildew.

Insects

The Lirac is susceptible to cabbage loopers, root aphids, green peach aphid, and lettuce aphid, and pea leafminer.

Physiological Stresses

The Lirac is susceptible to brown rib, tipburn, salt, and heat. It is moderately resistant/susceptible to drought and cold.

Post Harvest Stress

The Lirac is susceptible to pink rib, russet spotting, rusty brown discoloration, internal rib necrosis, and brown stain.

Apache

The standard regional check variety used is Apache.

Plant Type

Apache is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 1/9×10. The apical margin is moderately dentate. The basal margin is moderately dentate. The undulation is medium. The green color is medium green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin are strong. The green color is medium green.

The anthocyanin distribution is throughout and the concentration is intense. It is medium in size. It is glossy. Blistering is moderate. The leaf is thin. The trichomes are present.

Plant

The spread of frame leaves is 19 cm. The head diameter is 16 cm. The head shape is non-heading. The head weight is 240 g. The head firmness is loose. The butt is slightly concave. The midrib is flattened. The diameter at base of head is 16 mm. The ratio of head diameter/core diameter is 11.4. The core height from base of head to apex is 60 mm.

Bolting

The number of days from first water date to seed stalk emergence was 43. The bolting class is medium. The height of mature seed stalk is 65. The spread of bolter plant is 27 cm. The bolter leaves are straight. The margin is entire. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 29 days.

Viral Diseases

The Apache is susceptible to lettuce mosaic, cucumber mosaic, tomato bushy stunt, turnip mosaic, lettuce infectious yellows, beet western yellows, and big vein.

Fungal/Bacterial Diseases

The Apache is susceptible to corky root rot, botrylis, bacterial leaf spot, powdery mildew, anthracnose, bacterial soft rot, and sclerotinla drop. It is moderately susceptible/moderately resistant to verticillium wilt and to the CAI-CAVI races of downy mildew.

Insects

The Apache is susceptible to cabbage loopers, root aphids, green peach aphid, and lettuce aphid, and pea leafminer.

Physiological Stresses

The Apache is susceptible to brown rib. It is moderately susceptible/moderately resistant to tipburn, heat, drought, cold, and salt.

Post Harvest Stress

The Apache is susceptible to russet spotting, rusty brown discoloration, internal rib necrosis, brown stain, and pink rib.

ISI 43541

ISI 43541 is a red leaf lettuce variety developed from a hand pollinated cross of the varieties ISI 44038 and ISI 43117, both available from our genetical material. The initial cross was made in Fidenza (PR), Italy. The F1 seed harvested was designated as 33-0601053. The cross was made to produce a variety with dark red brilliant colour, upright standing, smooth leaves, good resistance against mildew, white seeds.

The following year, approximately 30 plants of the F1 seed were planted in Cesena (FC), Italy for seed increase, The block was roughed eliminating the self pollination plants. The F2 seed was harvested individually.

More than 20 F2 populations were planted in a research and development field trial in Cesena (FC), Italy the following year. Individual F2 plants were selected at market maturity for particular distinguishing characteristics in type, size, dark red brilliant colour, days to bolting, upright standing, smooth leaf, resistance against mildew, white seeds.

The F3 seed were trialed throughout the growing season in years 3 and 4 in Fidenza (PR), Italy.

A selected line was increased in year 5 in removing early bolting, less darker and bubbled plants and plants susceptible to mildew. The plants were harvested individually and the F5 population showed a good stability and uniformity.

The F6 seed was uniform and without variants and showed good bolting resistance. ISI 43541 was evaluated uniform and stable in commercial trials and seed production for two years.

Objective Description of the Variety ISI 43541

Plant Type

ISI 43541 is plant type Cutting/Leaf.

Seed

The seeds are white in color. The seeds do not require light. The seeds are not susceptible to heat dormancy.

Cotyledon to Fourth Leaf Stage

The cotyledons are broad in shape. The shape of the fourth leaf is elongated. The length/width index of the fourth leaf is 2/6×10. The apical margin is moderately dentate. The basal margin is moderately dentate. The undulation is medium. The green color is light green. The distribution of the anthocyanin is throughout and the concentration is intense. Rolling is absent. It is uncupped. There is no reflexing.

Mature Leaves

Margin

The incision depth is absent/shallow. The indentation is shallowly dentate. The undulations of the apical margin are strong. The green color is light green.

The anthocyanin distribution is throughout and the concentration is intense. It is medium in size. It is glossy. Blistering is absent/slight. The leaf is thin. The trichomes are absent.

Plant

The spread of frame leaves is 19 cm. The head diameter is 20 cm. The head shape is non-heading. The head firmness is loose. The butt is slightly concave. The midrib is moderately raised. The diameter at base of head is 13 mm. The ratio of head diameter/core diameter is 15.4. The core height from base of head to apex is 37 mm.

Bolting

The number of days from first water date to seed stalk emergence was 39. The bolting class is medium. The height of mature seed stalk is 75. The spread of bolter plant is 35 cm. The bolter leaves are straight. The margin is entire. The color is light green. The bolter habit of the terminal inflorescence is absent. The bolter habit of the lateral shoots is present. The bolter habit of the basal side shoots is absent.

Maturity

The season picked was summer. The earliness of harvest-mature head formation was 25 days.

Adaptation

The primary region of adaptation was Southwest. ISI 43541 adapted in the Southwest in the spring, summer, and fall seasons. The soil type was both organic and mineral.

Viral Diseases

ISI 43541 is moderately susceptible/moderately resistant to big vein, lettuce mosaic, and beet western yellows. It is susceptible to cucumber mosaic, tomato bushy stunt, turnip mosaic, and lettuce infectious yellows.

Fungal/Bacterial Diseases

ISI 43541 is moderately susceptible/moderately resistant to corky root rot, powdery mildew, sclerotinia drop, and verticillium wilt. It is susceptible to bacterial soft rot, botrytis, bacterial leaf spot and anthracnose. It is resistant to the CAI-CAVI races of downy mildew.

Insects

ISI 43541 is susceptible to cabbage loopers, root aphids, green peach aphid, lettuce aphid, and pea leafminer.

Physiological Stresses

ISI 43541 is susceptible to salt and brown rib. It is moderately susceptible/moderately resistant to cold, tipburn, and drought.

Post Harvest Stress

ISI 43541 is susceptible to pink rib, russet spotting, rusty brown discoloration, internal rib necrosis, and brown stain.

Comparisons to ISI 43541

Lirac

The most similar variety used as a comparison to ISI 43541 is Lirac.

Plant Type

Lirac is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/0×10. The apical margin is moderately dentate. The basal margin is moderately dentate. The undulation is medium. The green color is light green. The distribution of the anthocyanin is throughout. The concentration is moderate. Rolling is absent. It is uncupped. There is no reflexing.

Mature Leaves

Margin

The incision depth is absent/shallow. The indentation is shallowly dentate. The undulations of the apical margin are strong. The green color is light green.

The anthocyanin distribution is throughout and the concentration is moderate. It is medium in size. It is glossy. There is moderate blistering. The leaf is thin. The trichomes are absent.

Plant

The spread of frame leaves is 21 cm. The head diameter is 24 cm. The head shape is non-heading. The head firmness is loose. The butt is slightly concave. The midrib is moderately raised. The diameter at base of head is 14 mm. The ratio of head diameter/core diameter is 17.1. The core height from base of head to apex is 33 mm.

Bolting

The number of days from first water date to seed stalk emergence was 48. The bolting class is slow. The height of mature seed stalk is 65. The spread of bolter plant is 30 cm. The bolter leaves are straight. The margin is entire. The color is light green. The bolter habit of the terminal inflorescence is absent. The bolter habit of the lateral shoots is present. The bolter habit of the basal side shoots is absent.

Maturity

The season picked was summer. The earliness of harvest-mature head formation was 30 days.

Viral Diseases

The Lirac is susceptible to big vein, lettuce mosaic, cucumber mosaic, tomato bushy stunt, turnip mosaic, beet western yellows and lettuce infectious yellows.

Fungal/Bacterial Diseases

The Lirac is susceptible to corky root rot, botrylis, verticillium wilt, bacterial leaf spot, and anthracnose, powdery mildew, sclerotinla drop, and bacterial soft rot. It is moderately resistant/moderately susceptible to CAI-CAVI races of downy mildew.

Insects

The Lirac is susceptible to cabbage loopers, root aphids, green peach aphid, and lettuce aphid, and pea leafminer.

Physiological Stresses

The Lirac is susceptible to brown rib, tipburn, salt, and heat. It is moderately resistant/susceptible to drought and cold.

Post Harvest Stress

The Lirac is susceptible to pink rib, russet spotting, rusty brown discoloration, internal rib necrosis, and brown stain.

Apache

The standard regional check variety used is Apache.

Plant Type

Apache is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 1/9×10. The apical margin is moderately dentate. The basal margin is moderately dentate. The undulation is medium. The green color is medium green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin are strong. The green color is medium green.

The anthocyanin distribution is throughout and the concentration is intense. It is medium in size. It is glossy. Blistering is moderate. The leaf is thin. The trichomes are present.

Plant

The spread of frame leaves is 19 cm. The head diameter is 16 cm. The head shape is non-heading. The head weight is 240 g. The head firmness is loose. The butt is slightly concave. The midrib is flattened. The diameter at base of head is 16 mm. The ratio of head diameter/core diameter is 11.4. The core height from base of head to apex is 60 mm.

Bolting

The number of days from first water date to seed stalk emergence was 43. The bolting class is medium. The height of mature seed stalk is 65. The spread of bolter plant is 27 cm. The bolter leaves are straight. The margin is entire. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 29 days.

Viral Diseases

The Apache is susceptible to lettuce mosaic, cucumber mosaic, tomato bushy stunt, turnip mosaic, lettuce infectious yellows, beet western yellows, and big vein.

Fungal/Bacterial Diseases

The Apache is susceptible to corky root rot, botrylis, bacterial leaf spot, powdery mildew, anthracnose, bacterial soft rot, and sclerotinla drop. It is moderately susceptible/moderately resistant to verticillium wilt and to the CAI-CAVI races of downy mildew.

Insects

The Apache is susceptible to cabbage loopers, root aphids, green peach aphid, and lettuce aphid, and pea leafminer.

Physiological Stresses

The Apache is susceptible to brown rib. It is moderately susceptible/moderately resistant to tipburn, heat, drought, cold, and salt.

Post Harvest Stress

The Apache is susceptible to russet spotting, rusty brown discoloration, internal rib necrosis, brown stain, and pink rib.

Deposit Information

Applicants have made available to the public without restriction a deposit of at least 2500 seeds of lettuce variety ISI 43509 with the American Type Culture Collection (ATCC), P.O. Box 1549, MANASSAS, Va. 20108 USA, under the provisions of the Budapest Treaty with a deposit on Jul. 11, 2008, which has been assigned ATCC number PTA-9365.

Applicants have made available to the public without restriction a deposit of at least 2500 seeds of lettuce variety ISI 43541 with the American Type Culture Collection (ATCC), P.O. Box 1549, MANASSAS, Va. 20108 USA, under the provisions of the Budapest Treaty with a deposit on Jul. 11, 2008, which has been assigned ATCC number PTA-9366.

The invention claimed is:

1. A lettuce seed designated as ISI 43509 having ATCC Accession Number PTA-9365.

2. A lettuce plant produced by growing the seed of claim 1.

3. A plant part from the plant of claim 2.

4. The plant part of claim 3 wherein said part is a head.

5. The plant part of claim 3 wherein said part is a leaf or a portion thereof.

6. A lettuce plant having all the physiological and morphological characteristics of the lettuce plant of claim 2.

7. A plant part from the plant of claim 6.

8. The plant part of claim 7 wherein said part is a head.

9. The plant part of claim 7 wherein said part is a leaf or a portion thereof.

10. A $F_1$ hybrid lettuce plant having ISI 43509 as a parent where ISI 43509 is grown from the seed of claim 1.

11. Pollen of the plant of claim 2.

12. An ovule of the plant of claim 2.

13. A tissue culture of the plant of claim 2.

14. A method of making lettuce seeds comprised of crossing the plant of claim 2 with another lettuce plant and harvesting seed therefrom.

15. A method of making lettuce variety ISI 43509 by selecting seeds from the cross of one ISI 43509 plant with another ISI 43509 plant.

16. A lettuce seed designated as ISI 43541 having ATCC Accession Number PTA-9366.

17. A lettuce plant produced by growing the seed of claim 16.

18. A plant part from the plant of claim 17.

19. The plant part of claim 18 wherein said part is a head.

20. The plant part of claim 18 wherein said part is a leaf or a portion thereof.

21. A lettuce plant having all the physiological and morphological characteristics of the lettuce plant of claim 17.

22. A plant part from the plant of claim 21.

23. The plant part of claim 22 wherein said part is a head.

24. The plant part of claim 22 wherein said part is a leaf or a portion thereof.

25. A $F_1$ hybrid lettuce plant having ISI 43541 as a parent where ISI 43541 is grown from the seed of claim 16.

26. Pollen of the plant of claim 17.

27. An ovule of the plant of claim 17.

28. A tissue culture of the plant of claim 17.

29. A method of making lettuce seeds comprised of crossing the plant of claim 17 with another lettuce plant and harvesting seed therefrom.

30. A method of making lettuce variety ISI 43541 by selecting seeds from the cross of one ISI 43541 plant with another ISI 43541 plant.

* * * * *